(12) United States Patent
Osawa

(10) Patent No.: US 11,950,899 B2
(45) Date of Patent: Apr. 9, 2024

(54) MONITORING SYSTEM

(71) Applicant: NIDEC COPAL CORPORATION, Tokyo (JP)

(72) Inventor: Hideki Osawa, Tokyo (JP)

(73) Assignee: NIDEC COPAL CORPORATION, Tokyo (JP)

( * ) Notice: Subject to any disclaimer, the term of this patent is extended or adjusted under 35 U.S.C. 154(b) by 52 days.

(21) Appl. No.: 17/892,120

(22) Filed: Aug. 22, 2022

(65) Prior Publication Data

US 2023/0065340 A1 Mar. 2, 2023

(30) Foreign Application Priority Data

Aug. 26, 2021 (JP) .................. 2021-137914

(51) Int. Cl.
| | |
|---|---|
| A61B 5/11 | (2006.01) |
| H04B 17/318 | (2015.01) |
| H04W 4/021 | (2018.01) |
| H04W 4/33 | (2018.01) |
| H04W 4/80 | (2018.01) |

(52) U.S. Cl.
CPC .......... *A61B 5/1113* (2013.01); *H04B 17/318* (2015.01); *H04W 4/021* (2013.01); *H04W 4/33* (2018.02); *H04W 4/80* (2018.02)

(58) Field of Classification Search
CPC ..... A61B 5/1113; H04B 17/318; H04W 4/33; H04W 4/80; H04W 4/021

USPC .................................................... 340/539.12
See application file for complete search history.

(56) References Cited

U.S. PATENT DOCUMENTS

| | | | | |
|---|---|---|---|---|
| 2015/0247913 | A1* | 9/2015 | Messier | G01S 5/0027 340/539.13 |
| 2016/0295376 | A1* | 10/2016 | Geng | H04W 4/021 |
| 2016/0324460 | A1* | 11/2016 | Kusens | A61B 5/1128 |
| 2023/0065340 | A1* | 3/2023 | Osawa | A61B 5/1113 |

FOREIGN PATENT DOCUMENTS

JP 2019144120 A 8/2019

* cited by examiner

*Primary Examiner* — Kam Wan Ma
(74) *Attorney, Agent, or Firm* — HAUPTMAN HAM, LLP

(57) ABSTRACT

A monitoring system can protect the privacy of a treatment recipient while monitoring the treatment recipient being treated. A transmitter transmits a beacon signal. A beacon detector detects an RSSI(2) of the beacon signal. A monitoring device includes an imaging element, an open-close body, a beacon detector, an obtainer, and an open-close body controller. The imaging element captures an image of a treatment recipient being treated by a treatment provider through an opening. The open-close body opens and closes the opening. The beacon detector detects an RSSI(1) of the beacon signal. The obtainer obtains the RSSI(2) detected by the beacon detector. The open-close body controller controls opening and closing of the open-close body based on the RSSI(1) detected by the beacon detector and the RSSI(2) obtained by the obtainer.

6 Claims, 9 Drawing Sheets

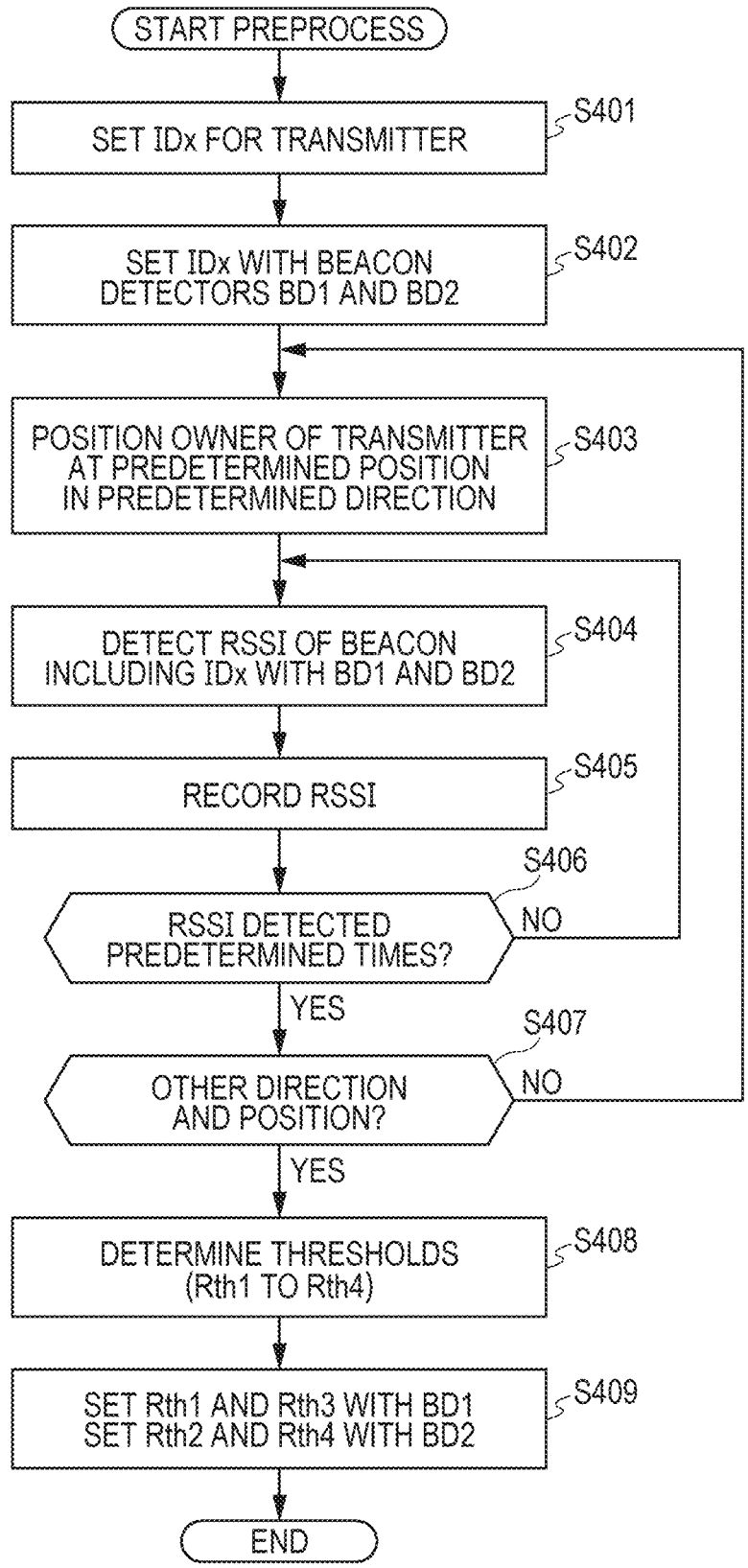

MONITORING SYSTEM

RELATED APPLICATIONS

The present application claims priority to Japanese Application Number 2021-137914, filed Aug. 26, 2021, the disclosure of which is hereby incorporated by reference herein in its entirety.

BACKGROUND

Technical Field

The present invention relates to a monitoring system.

Description of the Background

Patent Literature 1 describes an indoor position estimation method for deriving accurate positional information about a mobile terminal at a position from radio wave intensity measured by the mobile terminal based on a predetermined indoor radio wave intensity distribution. More specifically, radio wave intensity from a transmitter installed stationary is measured at known multiple measurement positions in a preliminary step. The intensity distribution of indoor radio waves is predetermined from the measurement results using a radial basis function. In an actual use, the position of the mobile terminal is estimated based on the radio wave intensity measured by the mobile terminal and the radio wave intensity distribution obtained in the preliminary step.

CITATION LIST

Patent Literature

Patent Literature 1: Japanese Unexamined Patent Application Publication No. 2019-144120

BRIEF SUMMARY

To record any troubles in medical facilities and welfare facilities, for example, treatment recipients such as patients and care recipients being treated by treatment providers such as doctors, nurses, and carers are to be monitored with surveillance cameras. However, constantly monitoring such treatment recipients with surveillance cameras may deteriorate privacy protection of the treatment recipients. In particular, the treatment recipients can be under great stress when visually recognizing that the surveillance cameras are capturing their images.

One aspect of the present invention is directed to a monitoring system that can protect the privacy of a treatment recipient while monitoring the treatment recipient being treated.

A monitoring system according to an aspect of the present invention includes a transmitter to be carried by a treatment provider to treat a treatment recipient in a room, a monitoring device placeable nearer a doorway of the room than a treatment location at which the treatment recipient is to be treated, and a second beacon detector placeable nearer the treatment location than the monitoring device. The transmitter transmits a beacon signal. The second beacon detector detects a second received signal strength indicator of the beacon signal from the transmitter. The monitoring device includes an imaging element, an open-close body, a first beacon detector, an obtainer, and an open-close body controller. The imaging element captures an image of the treatment recipient being treated by the treatment provider through an opening. The open-close body opens and closes the opening. The first beacon detector detects a first received signal strength indicator of the beacon signal from the transmitter. The obtainer obtains the second received signal strength indicator detected by the second beacon detector. The open-close body controller controls opening and closing of the open-close body based on the first received signal strength indicator detected by the first beacon detector and the second received signal strength indicator obtained by the obtainer.

The monitoring system according to the above aspect of the present invention can protect the privacy of a treatment recipient while monitoring the treatment recipient being treated.

BRIEF DESCRIPTION OF DRAWINGS

FIG. 10 is a flowchart of an example preprocess performed before the processes in FIGS. 7 to 9.

DETAILED DESCRIPTION

Figure 1:
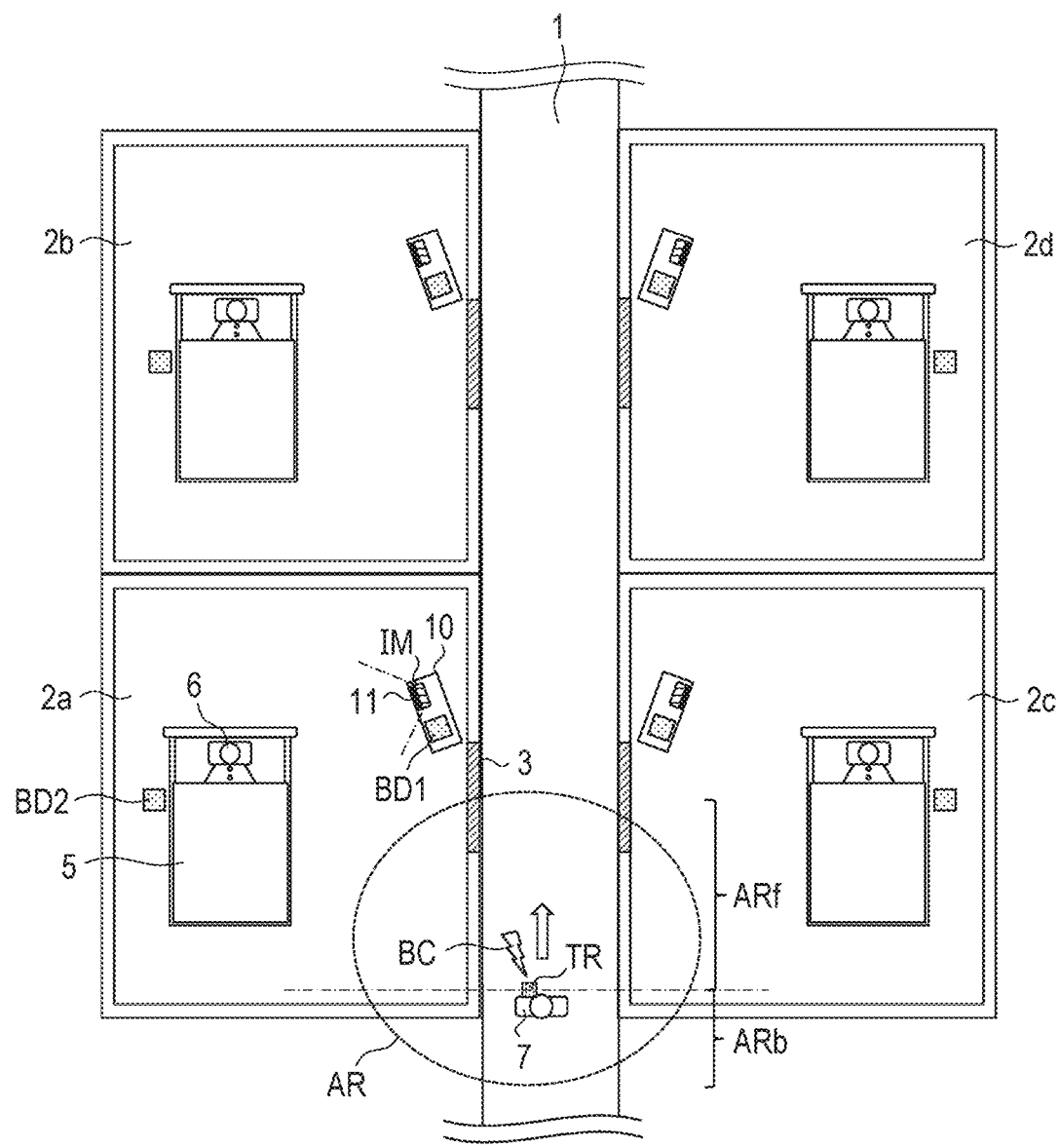
FIG. 1 is a schematic diagram of a monitoring system according to one embodiment showing an example structure and an example use.

One or more embodiments of the present invention will now be described in detail with reference to the drawings. Throughout the drawings describing one or more embodiments, like reference numerals basically denote like components. Such components will not be described repeatedly.

Overview of Monitoring System

FIG. 1 is a schematic diagram of a monitoring system according to one embodiment showing an example structure and an example use. FIG. 1 illustrates a facility including two moms 2a and 2b on one side of a corridor 1 and two rooms 2c and 2d on the other side of the corridor 1. The facility is, for example, a medical facility or a welfare facility. In FIG. 1, a treatment provider 7 walks down the corridor 1 with a transmitter TR, for example, in a front pocket or attached to a neck strap.

The transmitter TR transmits a beacon signal BC in a transmission area AR. The beacon signal BC is detectable in the transmission area AR. The transmission area AR refers to an area in which a received signal strength indicator (RSSI) is high enough for receiving the beacon signal BC. The transmission area AR is ideally a circular area around the transmitter TR. The RSSI is gradually lower from the center of the circle toward the periphery.

However, the beacon signal BC can be actually interfered by the body of the treatment provider 7. Thus, the transmission area AR is not circular. More specifically, a rear transmission area ARb behind the treatment provider 7 can be smaller than a front transmission area ARf in front of the treatment provider 7.

In an example of the room 2a, a bed 5, a monitoring device 10, and a beacon detector BD2 are installed in the room 2a. The monitoring device 10 and the beacon detector BD2 are included in the monitoring system together with the transmitter TR. A treatment recipient 6 is lying on the bed 5. The treatment provider 7 enters the room 2a through a doorway 3 and treats the treatment recipient 6 at a treatment location, or on the bed 5 in this example, in the room 2a. The monitoring device 10 is located nearer the doorway 3 of the room 2a than the treatment location, or the bed 5. In this example, the monitoring device 10 is located adjacent to the doorway 3.

The monitoring device 10 includes an imaging unit IM, a beacon detector BD1, and an open-close body 11. The imaging unit IM includes an imaging element (not shown) that captures an image through an opening in the imaging unit IM. The open-close body 11 covers and uncovers the opening in the imaging unit IM. The open-close body 11 may be any component that can cover and uncover the opening, such as a shutter, a barrier, or a cover. In the embodiment, the open-close body 11 is a shutter. The imaging element in the imaging unit IM captures an image of the entire room 2a including the treatment recipient 6 being treated by the treatment provider 7 when the treatment provider 7 is in the room 2a.

In this manner, any troubles associated with the action of the treatment provider 7 in the room 2a can be recorded with the monitoring device 10, including the treatment provided to the treatment recipient 6. However, constantly capturing an image of the treatment recipient 6 with the imaging unit IM can deteriorate privacy protection of the treatment recipient 6. In particular, the treatment recipient 6 can be under great stress when visually recognizing that the imaging unit IM is capturing an image of the treatment recipient 6. Thus, when the treatment provider 7 is not in the room 2a, image capturing with the imaging unit IM is to be suspended, and this suspension of the image capturing is to be visually clearly recognized by the treatment recipient 6.

A shutter as the open-close body 11 is thus used. When the treatment provider 7 is in the room 2a, the shutter 11 uncovers the opening to enable image capturing. When the treatment provider 7 is not in the room 2a, the shutter 11 covers the opening to disable image capturing and allows the treatment recipient 6 to visually recognize that the image capturing is disabled. To control the opening and closing of the shutter 11 in this manner, at least one beacon detector BD2 is used, in addition to the beacon detector BD1 in the monitoring device 10.

Figure 2A:
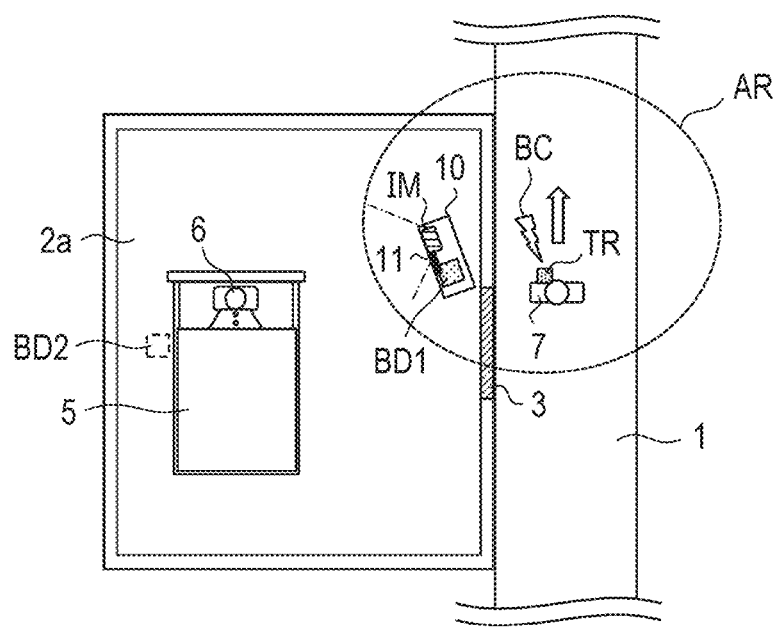
FIG. 2A is a schematic diagram of a monitoring system according to a comparative example of the monitoring system in FIG. 1 describing an example issue.
Figure 2B:
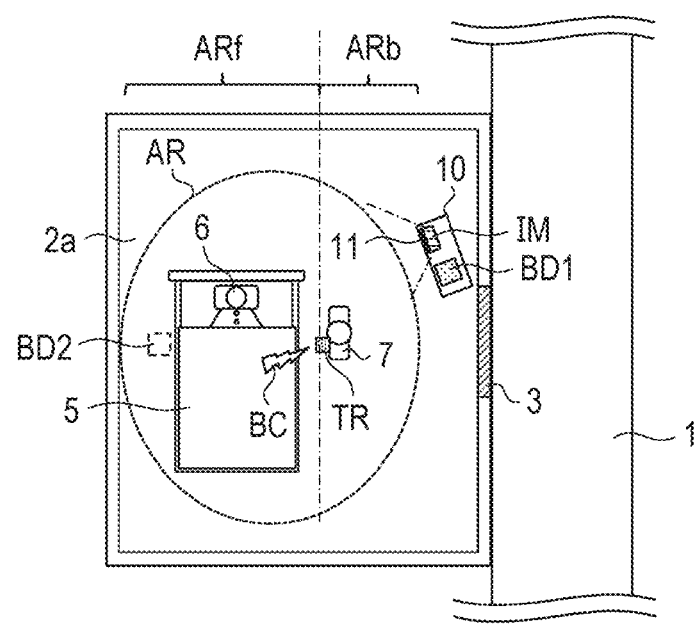
FIG. 2B is a schematic diagram of the monitoring system according to the comparative example of the monitoring system in FIG. 1 describing another example issue.

The beacon detector BD1 detects an RSSI(1) of the beacon signal BC from the transmitter TR. Similarly, the beacon detector BD2 detects an RSSI(2) of the beacon signal BC from the transmitter TR. The beacon detector BD2 is located nearer the treatment location at which the treatment recipient 6 is treated, or the bed 5 than the monitoring device 10, or more specifically, the beacon detector BD1. In this example, the beacon detector BD2 is located adjacent to the bed 5. The monitoring device 10 controls opening and closing of the shutter 11 based on the RSSI(1) and the RSSI(2). More specifically, the monitoring device 10 determines whether the treatment provider 7 is in the mom 2a based on the RSSI(1) and the RSSI(2). Monitoring System in Comparative Example and Its Issues FIGS. 2A and 2B are schematic diagrams of a monitoring system according to a comparative example of the monitoring system in FIG. 1 describing its example issues. FIGS. 2A and 2B illustrate the room 2a in FIG. 1 and its surroundings. In the comparative example, for example, the monitoring system does not include the beacon detector BD2 in FIG. 1. In this case, for example, the monitoring device 10 is to open the shutter 11 while detecting the beacon signal BC using the beacon detector BD1, and to close the shutter 11 while detecting no beacon signal BC.

However, as shown in FIG. 2A, the treatment provider 7 may not enter the mom 2a and may pass by the doorway 3 of the room 2a while walking down the corridor 1. In this case as well, the monitoring device 10 can detect the beacon signal BC using the beacon detector BD1. The monitoring device 10 may thus control the shutter 11 to open when the treatment provider 7 is simply walking down the corridor 1.

As shown in FIG. 2B, the treatment provider 7 may treat the treatment recipient 6 near the bed 5 with the back of the treatment provider 7 facing the monitoring device 10. In this case, as described with reference to FIG. 1, the rear transmission area ARb is smaller than the front transmission area ARf, and thus the beacon detector BD1 may not detect the beacon signal BC. Thus, the monitoring device 10 may control the shutter 11 to close when the treatment recipient 6 is being treated.

In another comparative example, for example, the monitoring system does not include the beacon detector BD1 in FIG. 1. In this case, for example, the monitoring device 10 is to open the shutter 11 while detecting the beacon signal BC using the beacon detector BD2, and to close the shutter 11 while detecting no beacon signal BC.

Figure 3A:
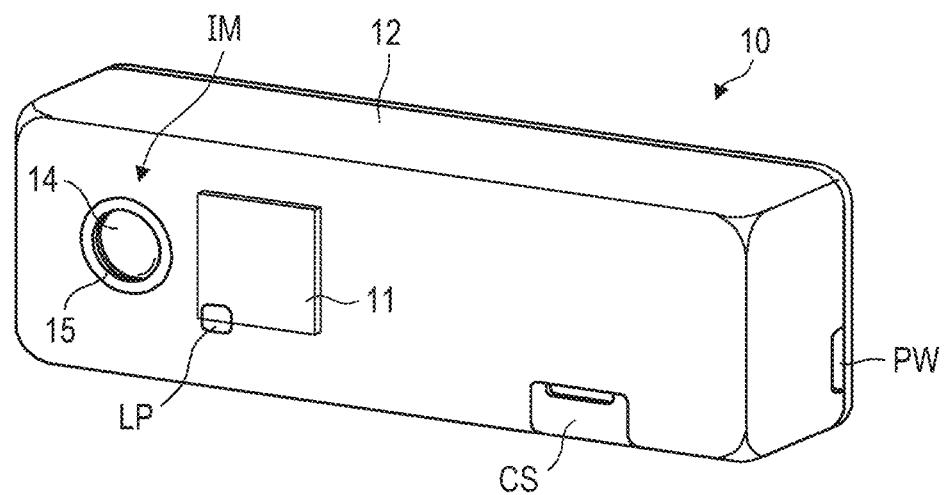
FIG. 3A is a perspective view of a monitoring device in FIG. 1 showing its example outer shape.
Figure 3B:
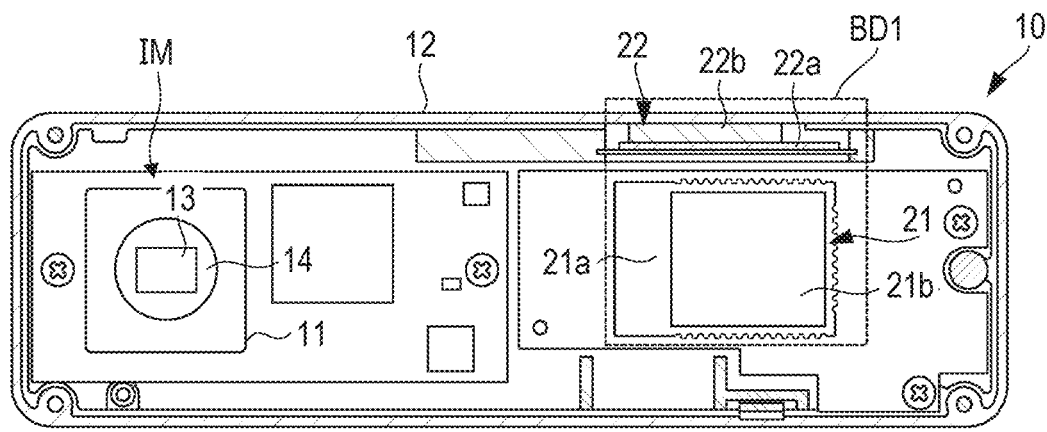
FIG. 3B is a plan view of the monitoring device in FIG. 3A showing an example outer shape of its internal structure.

Although not shown, the treatment provider 7 staying in the mom 2a may move to face in a different direction or may move away from the location at which the treatment recipient 6 is treated, or specifically from the bed 5. In this case, the beacon detector BD2 may not detect the beacon signal BC for a certain period of time. Thus, the monitoring device 10 may control the shutter 11 to close when the treatment provider 7 stays in the room 2a. As described in detail later, two or more beacon detectors BD1 and BD2 are thus used to control the opening and closing of the shutter 11 based on detection results from the beacon detectors BD1 and BD2. Details of Monitoring System FIG. 3A is a perspective view of the monitoring device in FIG. 1 showing its example outer shape. FIG. 3B is a plan view of the monitoring device in FIG. 3A showing an example outer shape of its internal structure. As shown in FIG. 3A, the monitoring device 10 includes a substantially rectangular housing 12. As shown in FIGS. 3A and 3B, the housing 12 of the monitoring device 10 accommodates an imaging unit IM, or in other words, an imaging element 13 and a lens 14 included in a surveillance camera. The imaging element 13 is a charge-coupled device (CCD) image sensor or a complementary metal-oxide semiconductor (CMOS) image sensor. The lens 14 focuses light from a subject on the imaging element 13.

As shown in FIG. 3A, the housing 12 has an opening 15 for allowing light to enter the imaging element 13 through the lens 14. The shutter (open-close body) 11 for covering and uncovering the opening 15 is attached to the housing 12 in a movable manner. The shutter 11 moves to a position to uncover the opening 15 as shown in FIG. 3A while image capturing with the imaging unit IM is being performed. The shutter 11 moves to a position to cover the opening 15 as shown in FIG. 3B while image capturing with the imaging unit IM is suspended. The imaging unit IM may not include the lens 14.

As shown in FIG. 3A, the housing 12 includes, for example, a lamp LP that turns on during image capturing, a card slot CS for receiving a memory card, and a power supply port PW to which a power supply cable is connected. As shown in FIGS. 3A and 3B, the housing 12 accommodates two wireless communication modules 21 and 22. The two wireless communication modules 21 and 22 are included in the beacon detector BD1.

The wireless communication module 21 includes a printed circuit board 21a including an antenna and an integrated circuit component 21b mounted on the printed circuit board 21a. The wireless communication module 22 includes a printed circuit board 22a including an antenna and an integrated circuit component 22b mounted on the printed circuit board 22a. The integrated circuit components 21b and 22b include various wireless communication circuits such as a radio frequency (RF) circuit for modulating transmission radio waves and demodulating received radio waves and a power divider for generating transmission radio waves with a predetermined radio wave intensity. In this example, the two printed circuit boards 21a and 22a and the two antennas are located in the housing 12 in directions orthogonal to each other. This maintains the sensitivity of the antennas independently of the polarization direction of radio waves.

Figure 4:
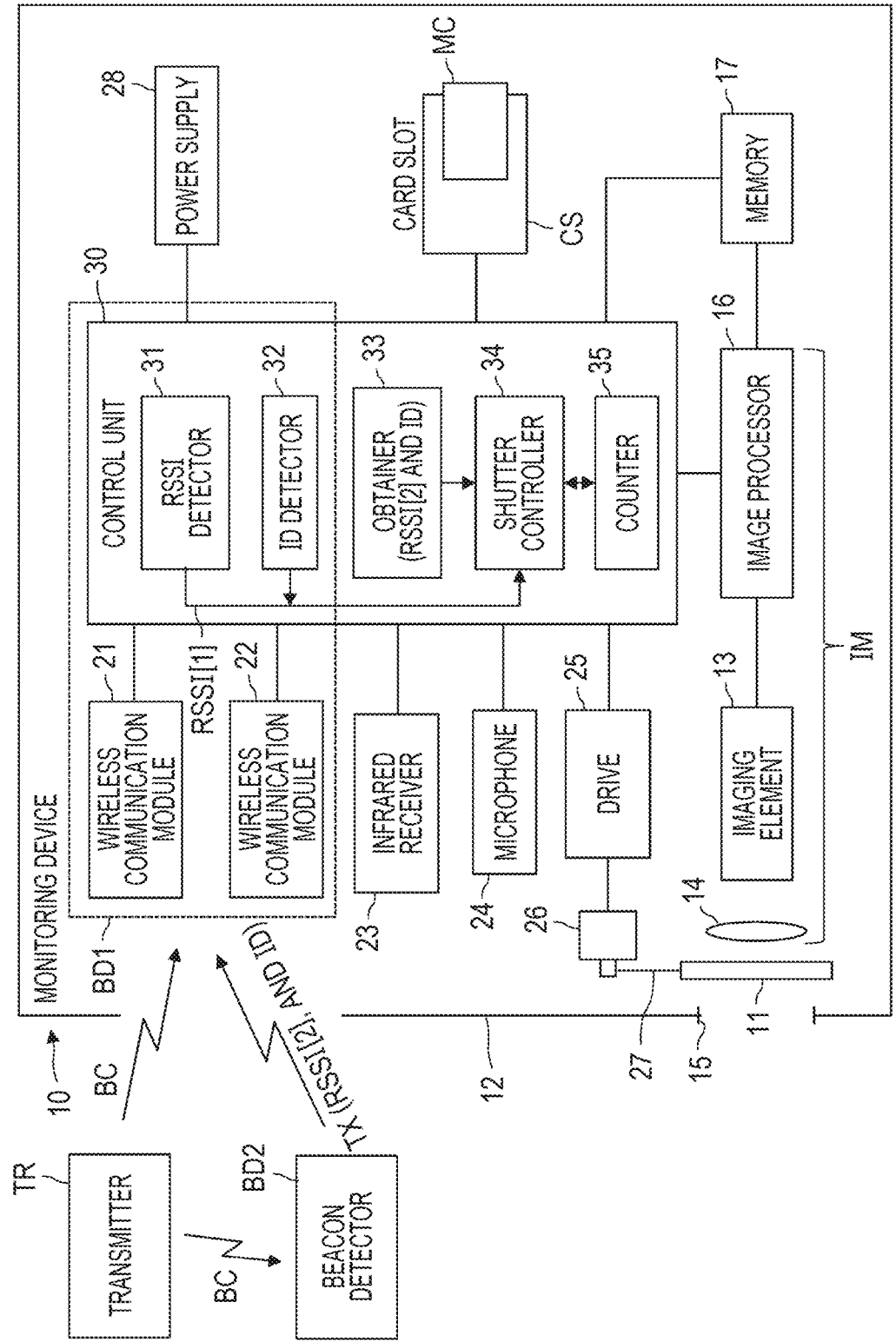
FIG. 4 is a functional block diagram of the monitoring device in FIG. 1 showing its main components.

FIG. 4 is a functional block diagram of the monitoring device in FIG. 1 showing its main components. The monitoring device 10 shown in FIG. 4 includes the shutter 11, the imaging unit IM, a memory 17, the wireless communication modules 21 and 22, an infrared receiver 23, a microphone 24, a drive 25, a control unit 30, a power supply 28, and the card slot CS. The memory 17 is a combination of a volatile memory such as a random-access memory (RAM) and a nonvolatile memory such as a flash memory, a solid-state drive (SSD), or a hard disk drive (HDD).

The control unit 30 includes, for example, a microcontroller including a processor and various peripheral circuits. In this case, a part of the memory 17 is also mounted on the microcontroller. The control unit 30 controls the entire monitoring device 10. The control unit 30 may not include the microcontroller, and may include, for example, a field-programmable gate array (FPGA) or an application-specific integrated circuit (ASIC).

The imaging unit IM includes an image processor 16 in addition to the imaging element 13 and the lens 14 described above. As described with reference to FIG. 1, the imaging element 13 captures, through the opening 15, an image of the entire room 2a including the treatment recipient 6 being treated by the treatment provider 7. The image processor 16 is, for example, an image signal processor (ISP). The image processor 16 converts image data, or more specifically, raw data from the imaging element 13 to image data in a predetermined format including a red-green-blue (RGB) format and stores the image data into the memory 17.

The wireless communication modules 21 and 22 receive, from the transmitter TR, the beacon signal BC complying with a predetermined wireless communication standard. The beacon signal BC may comply with, for example, the Bluetooth Low Energy (BLE, registered trademark) standard, the radio frequency identification (RFID) standard, or the ZigBee (registered trademark) standard. In the embodiment, the beacon signal BC complying with the BLE standard is used to reduce the power consumption of the transmitter TR.

The wireless communication modules 21 and 22 receive, from the beacon detector BD2, a transmission signal TX complying with a predetermined wireless communication standard. The beacon detector BD2 detects the RSSI(2) and an identifier (ID) of the beacon signal BC and transmits the transmission signal TX including the detected RSSI(2) and ID to the wireless communication modules 21 and 22. In the embodiment, the transmission signal TX complying with the BLE standard is used similarly to the beacon signal BC. Another wireless communication standard including Wi-Fi (registered trademark) may be used for communication between the monitoring device 10 and the beacon detector BD2. The monitoring device 10 and the beacon detector BD2 may not communicate with each other wirelessly, and may communicate with each other in a wired manner.

The infrared receiver 23, for example, receives an infrared command from a remote controller and transmits the command to the control unit 30. The microphone 24 detects a voice. The detected voice may be, for example, stored into the memory 17 with the control unit 30 or used when the control unit 30 performs various control operations based on voice recognition.

The power supply 28 includes, for example, a power management integrated circuit (IC). The power supply 28 receives power from the power supply port PW shown in FIG. 3A and supplies power to each component in the monitoring device 10 at a predetermined power supply voltage. The power supply 28 controls power supply to each component in response to a command from the control unit 30. In one example, the power supply 28 may perform power saving control by cutting power supply to components that use no power when no image capturing is performed. The power supply 28 may not receive power from the power supply port PW, but may receive power from a battery.

The card slot CS receives a memory card MC, which is accessible by the control unit 30. The control unit 30 can, for example, copy the image data stored in the memory 17 by the imaging unit IM to the memory card MC.

The control unit 30 includes, for example, an RSSI detector 31, an ID detector 32, an obtainer 33, and a shutter controller 34 that are implemented by the processor executing a program stored in a memory, and a counter 35. The RSSI detector 31 and the ID detector 32 are included in the beacon detector BD1 together with the wireless communication modules 21 and 22.

The RSSI detector 31 detects the RSSI(1) of the beacon signal BC from the transmitter TR through, for example, the wireless communication modules 21 and 22 and an analog-to-digital converter. The ID detector 32 detects the ID included in the beacon signal BC to identify the transmitter TR and the treatment provider 7. The obtainer 33 obtains the RSSI(2) and the ID detected by the beacon detector BD2 based on the transmission signal TX received by the wireless communication modules 21 and 22.

The shutter controller (open-close body controller) 34 generally controls opening and closing of the shutter (open-close body) 11 with the drive 25 based on the RSSI(1) detected by the RSSI detector 31, the ID detected by the ID detector 32, and the RSSI(2) and the ID obtained by the obtainer 33. In addition, the shutter controller 34 controls opening and closing of the shutter 11 using the counter 35 that counts a predetermined time (Tmax). In response to an opening or closing command from the shutter controller 34, the drive 25 drives the shutter 11 and opens or closes the shutter 11 with an actuator 26 and a link assembly 27.

Figure 5:
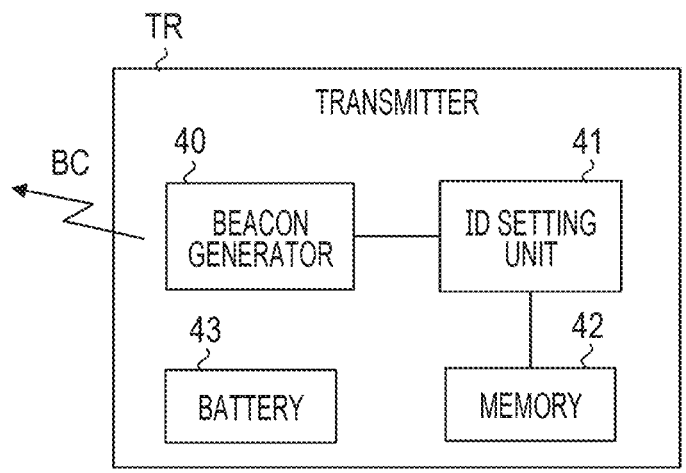
FIG. 5 is a functional block diagram of a transmitter in FIG. 1 showing its main components.

FIG. 5 is a functional block diagram of a transmitter in FIG. 1 showing its main components. The transmitter TR shown in FIG. 5 includes a beacon generator 40, an ID setting unit 41, a memory 42, and a battery 43. The memory 42 prestores, for example, ID information. The ID setting unit 41 sets an ID for the beacon signal BC based on the ID information stored in the memory 42. The beacon generator 40 transmits the beacon signal BC including the set ID. More specifically, the beacon generator 40 transmits the beacon signal BC complying with, for example, the BLE standard as described with reference to FIG. 4. The battery 43 supplies power to the entire transmitter TR. The ID setting unit 41 and the memory 42 may be implemented by, for example, a dual in-line package (DIP) switch.

For example, the transmitter TR is a mobile information terminal such as a smartphone, a mobile phone, or a personal handy-phone system (PHS). The ID information includes, for example, a serial number (international mobile equipment identity number, or IMEI number) and a phone number of the mobile information terminal in combination with a name and an employee number that identify the owner (treatment provider). The ID information is managed centrally by a central control device (not shown) in a format such as a list.

Figure 6:
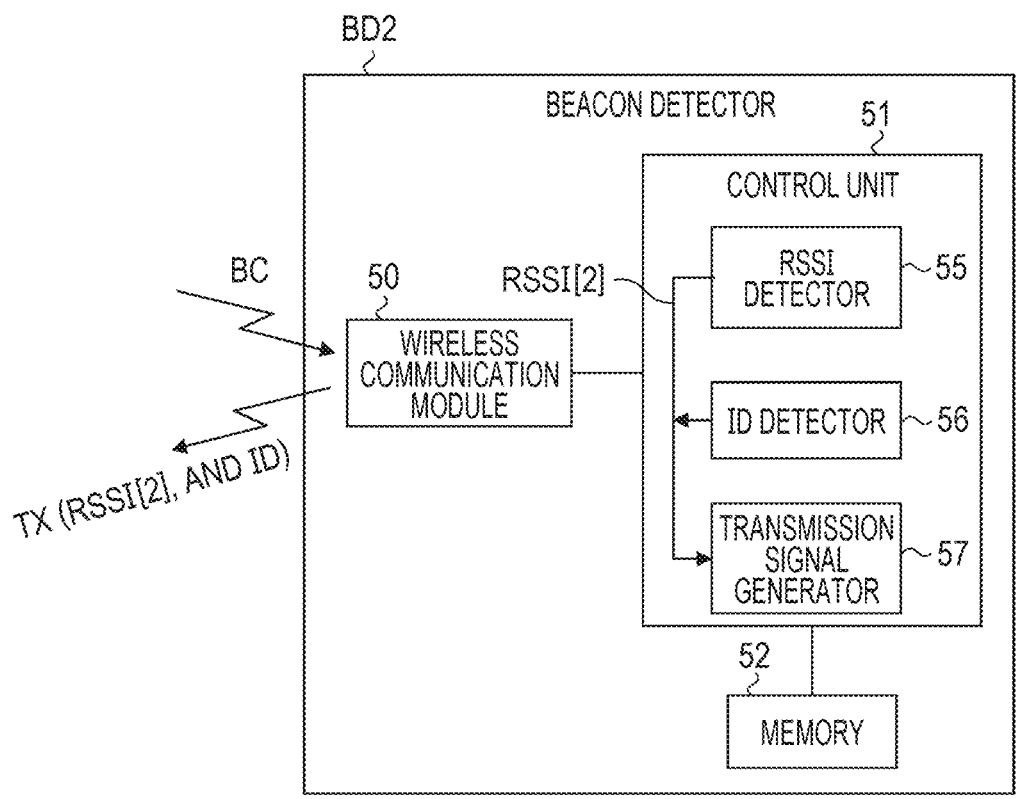
FIG. 6 is a functional block diagram of a beacon detector in FIG. 1 showing its main components.

FIG. 6 is a functional block diagram of a beacon detector in FIG. 1 showing its main components. The beacon detector BD2 shown in FIG. 6 includes a wireless communication module 50, a control unit 51, and a memory 52. The memory 52 is a combination of a volatile memory and a nonvolatile memory. Similarly to the wireless communication modules 21 and 22 in FIG. 4, the wireless communication module 50 receives, from the transmitter TR, the beacon signal BC complying with, for example, the BLE standard.

Similarly to the structure in FIG. 4, the control unit 51 includes, for example, a microcontroller. The control unit 51 includes, for example, an RSSI detector 55, an ID detector 56, and a transmission signal generator 57 that are implemented by a processor executing a program stored in the memory 52. The RSSI detector 55 detects the RSSI(2) of the beacon signal BC from the transmitter TR through, for example, the wireless communication module 50 and an analog-to-digital converter. The ID detector 56 detects the ID included in the beacon signal BC to identify the treatment provider 7.

The transmission signal generator 57 generates the transmission signal TX including the RSSI(2) detected by the RSSI detector 55 and the ID detected by the ID detector 56. The transmission signal generator 57 transmits the generated transmission signal TX to the wireless communication modules 21 and 22 in FIG. 4 through the wireless communication module 50. Similarly to the structure in FIG. 4, the wireless communication module 50 transmits the transmission signal TX complying with, for example, the BLE standard.

Details of Shutter Controller

Figure 7:
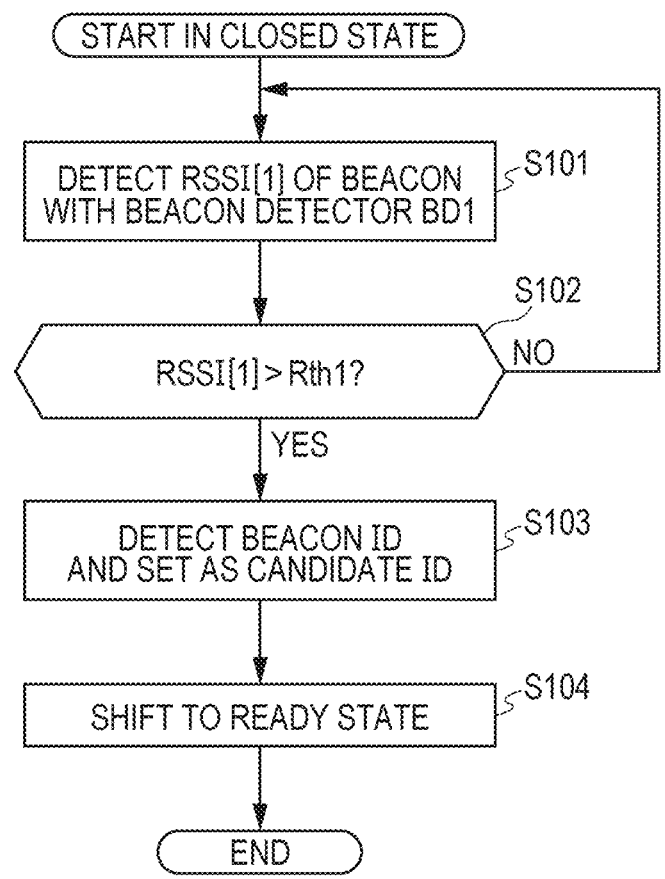
FIG. 7 is a flowchart of an example process performed by a shutter controller in FIG. 4 in a closed state.
Figure 8:
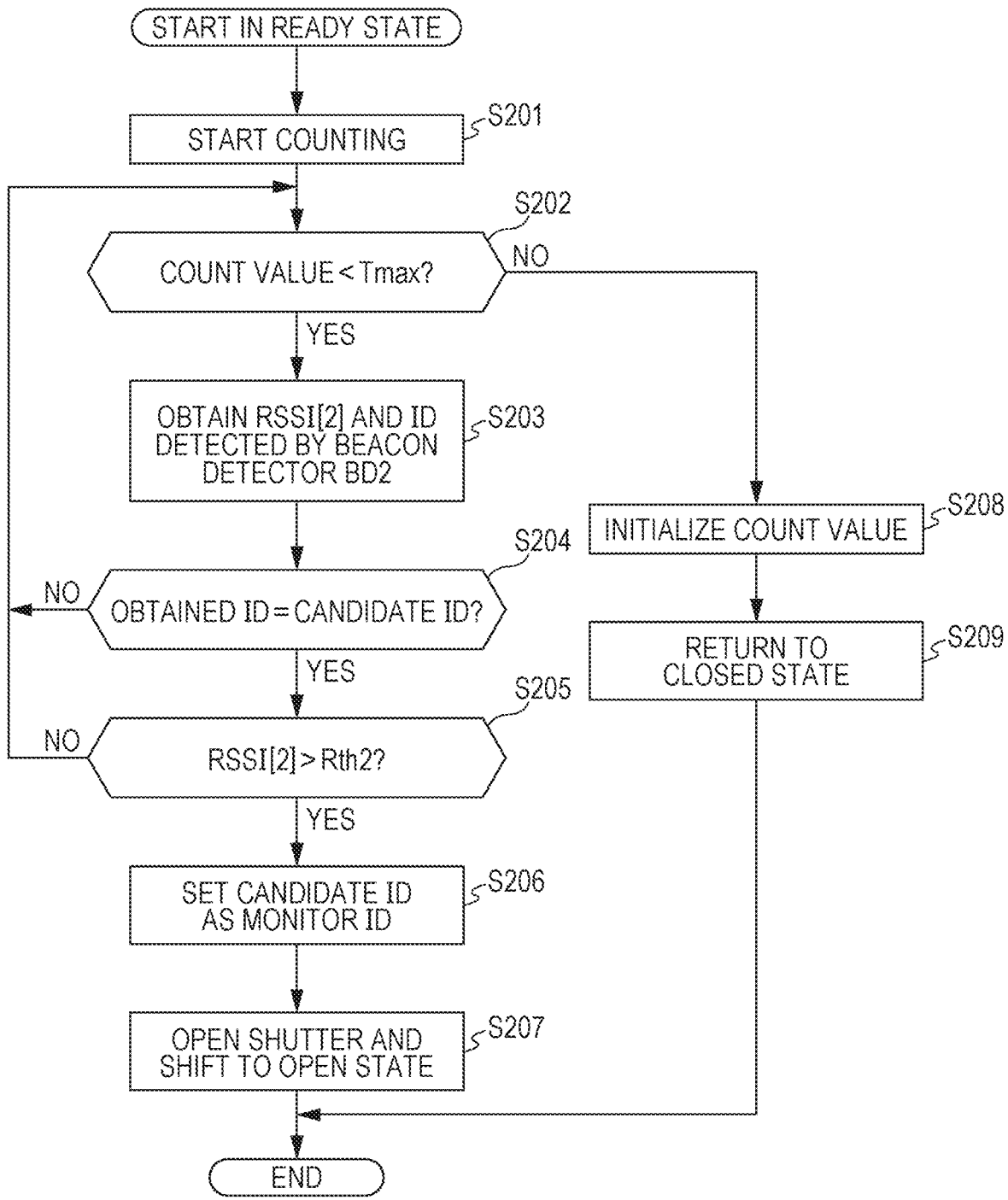
FIG. 8 is a flowchart of an example process performed by the shutter controller in FIG. 4 in a ready state.
Figure 9:
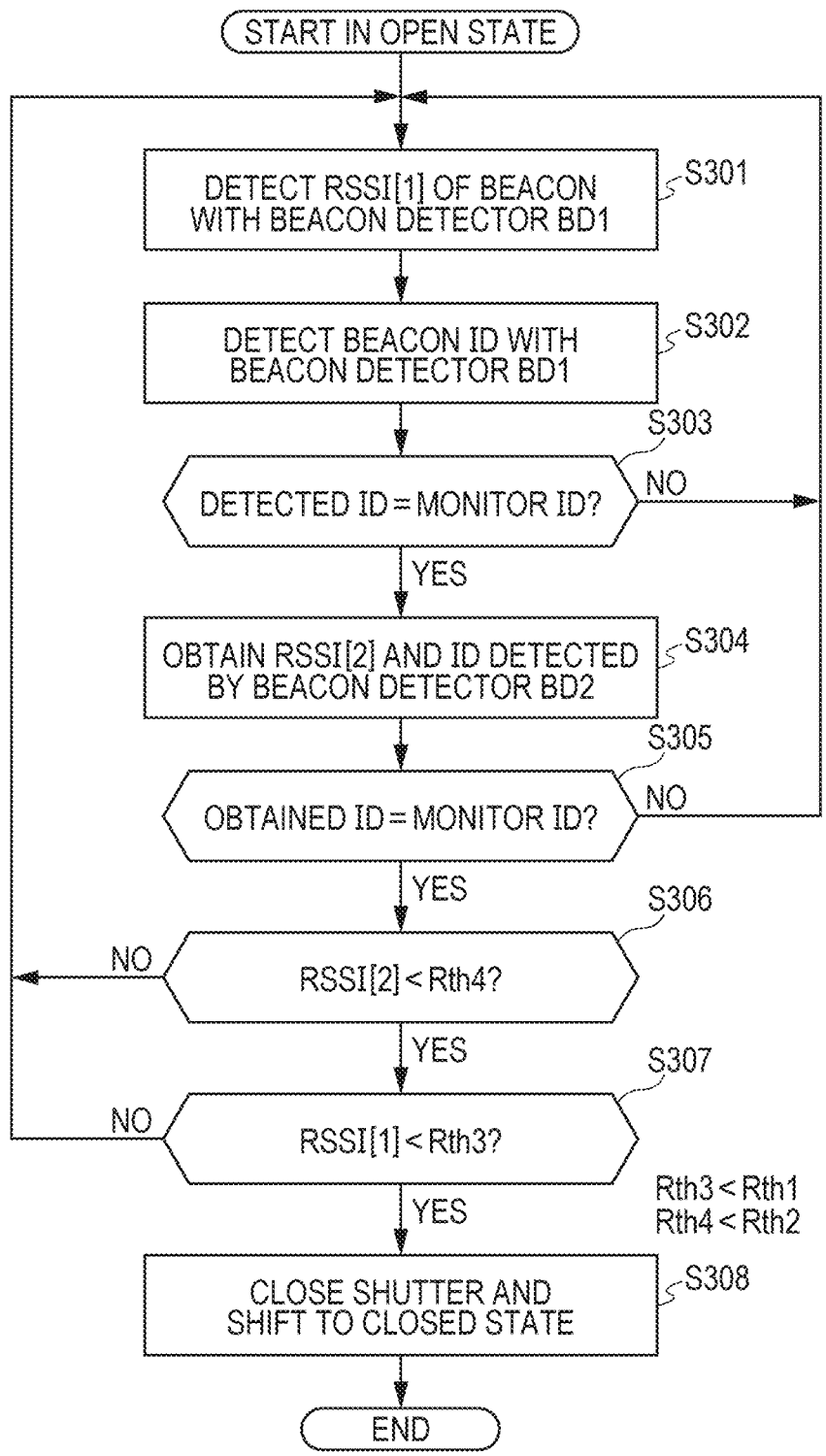
FIG. 9 is a flowchart of an example process performed by the shutter controller in FIG. 4 in an open state.

FIG. 7 is a flowchart of an example process performed by a shutter controller in FIG. 4 in a closed state. FIG. 8 is a flowchart of an example process performed by the shutter controller in FIG. 4 in a ready state. FIG. 9 is a flowchart of an example process performed by the shutter controller in FIG. 4 in an open state.

The shutter controller 34 is in a closed state, a ready state, or an open state as an internal control state. When the control state is the closed state, the shutter 11 is controlled to be closed. When the control state is the open state, the shutter 11 is controlled to be open. In the ready state, the determination is performed as to whether the control state is to shift from the closed state to the open state.

With the shutter 11 being closed, the shutter controller 34 performs the process in the closed state shown in FIG. 7 and then the process in the ready state shown in FIG. 8. In FIGS. 7 and 8, the shutter controller 34 generally opens the shutter 11 when the RSSI(2) detected by the beacon detector BD2 exceeds a threshold Rth2 within the predetermined time (Tmax) after the RSSI(1) detected by the beacon detector BD1 exceeds a threshold Rth1.

More specifically, in FIG. 7, the shutter controller 34 detects the RSSI(1) of the beacon signal BC using the beacon detector BD1, or more specifically, the RSSI detector 31 (step S101). Subsequently, the shutter controller 34 compares the detected RSSI(1) with the threshold Rth1 (step S102). The shutter controller 34 repeatedly performs the processing in steps S101 and S102 until the detected RSSI (1) exceeds the threshold Rth1 (No in step S102).

In response to the RSSI(1) exceeding the threshold Rth1 (Yes in step S102), the shutter controller 34 detects the ID of the beacon signal BC using the ID detector 32 and sets the detected ID as a candidate ID (step S103). The candidate ID is the ID of the transmitter that may possibly be brought into the room and the treatment provider 7 who may possibly enter the room. The shutter controller 34 then shifts from the closed state to the ready state in FIG. 8 (step S104).

In FIG. 8, the shutter controller 34 activates the counter 35 (step S201). Subsequently, the shutter controller 34 compares a count value of the counter 35 with the predetermined time Tmax (step S202). The time Tmax is determined as appropriate. The time Tmax is determined to be, for example, 20 seconds. When the count value has yet to exceed the time Tmax (Yes in step S202), the shutter controller 34 advances to step S203. When the count value has exceeded the time Tmax (No in step S202), the shutter controller 34 advances to step S208.

In step S203, the shutter controller 34 obtains, using the obtainer 33, the RSSI(2) and the ID detected by the beacon detector BD2. Subsequently, the shutter controller 34 determines whether the obtained ID is equal to the candidate ID set in step S103 in FIG. 7 (step S204). When the obtained ID is equal to the candidate 1D (Yes in step S204), the shutter controller 34 compares the obtained RSSI(2) with the threshold Rth2 (step S205).

When the obtained RSSI(2) is higher than the threshold Rth2 (Yes in step S205), the shutter controller 34 sets the candidate ID as a monitor ID (step S206). The monitor ID is the ID of the treatment provider 7 who has entered the room. The shutter controller 34 then opens the shutter 11 with the drive 25 and shifts to the open state to advance to step S301 in FIG. 9 (step S207). When the obtained RSSI(2) is lower than the threshold Rth2 (No in step S205) or when the obtained ID is different from the candidate ID (No in step S204), the shutter controller 34 returns to step S202.

The shutter controller 34 performs the processing in steps 203 to S205 again unless the count value exceeds the time Tmax. When the count value has exceeded the time Tmax (No in step S202), the shutter controller 34 stops the counter 35 and initializes the counter 35 (step S208). The shutter controller 34 shifts from the ready state to the closed state to return to step S101 in FIG. 7 (step S209).

With the shutter 11 being open, the shutter controller 34 performs the process in the open state shown in FIG. 9. In FIG. 9, the shutter controller 34 generally closes the shutter 1I when the RSSI(2) detected by the beacon detector BD2 falls below a threshold Rth4 and the RSSI(1) detected by the beacon detector BD1 falls below a threshold Rth3.

More specifically, in FIG. 9, the shutter controller 34 detects the RSSI(l) of the beacon signal BC using the beacon detector BD1, or more specifically, the RSSI detector 31 (step S301). Subsequently, the shutter controller 34 detects the ID of the beacon signal BC using the ID detector 32 (step S302). The shutter controller 34 then determines whether the detected ID is equal to the monitor ID set in step S206 in FIG. 8 (step S303).

When the detected ID is equal to the monitor ID (Yes in step S303), the shutter controller 34 obtains, using the obtainer 33, the RSSI(2) and the ID detected by the beacon detector BD2 (step S304). Subsequently, the shutter controller 34 determines whether the obtained ID is equal to the monitor ID (step S305).

When the obtained ID is equal to the monitor ID (Yes in step S305), the shutter controller 34 compares the RSSI(2) obtained in step S304 with the threshold Rth4 (step S306). When the RSSI(2) falls below the threshold Rth4 (Yes in step S306), the shutter controller 34 compares the RSSI(1) detected in step S301 with the threshold Rth3 (step S307).

When the detected RSSI(1) falls below the threshold Rth3 (Yes in step S307), the shutter controller 34 closes the shutter 11 with the drive 25 and shifts to the closed state to advance to step S101 in FIG. 7. When the detected RSSI(1) is higher than the threshold Rth3 (No in step S307) or when the obtained RSSI(2) is higher than the threshold Rth4 (No in step S306), the shutter controller 34 returns to step S301.

In this manner, the shutter controller 34 repeats the processing in steps S301 to S307 until the obtained RSSI(2) falls below the threshold Rth4 and the detected RSSI(1) falls below the threshold Rth3 described with reference to FIG. 7. The threshold Rth3 is set to a value less than the threshold Rth1. The threshold Rth4 is set to a value less than the threshold Rth2 described with reference to FIG. 8.

When the detected ID is different from the monitor ID (No in step S303) or when the obtained ID is different from the monitor ID (No in step S305), the shutter controller 34 returns to step S301. This corresponds to, for example, when the beacon detectors BD1 and BD2 detect the beacon signal BC from a new treatment provider 7. In this case, the shutter controller 34 waits until the RSSI(1) and the RSSI(2) of the beacon signal BC including the monitor ID are detected in the processing in steps S303 and S305.

The shutter controller 34 described above can determine whether the treatment provider 7 is in the room with high accuracy and appropriately control the opening and closing of the shutter 11. In a specific example, as shown in FIG. 2A, the treatment provider 7 passes by the doorway 3 of the room 2a while walking down the corridor 1. In this case, the determination result in step S102 in FIG. 7 is affirmative. However, the determination results in steps S204 and S205 in FIG. 8 are negative. Thus, the treatment provider 7 is determined not to have entered the room, and the shutter 11 remains closed.

In another example, the treatment provider 7 enters the room 2a through the doorway 3 and treats the treatment recipient 6 as shown in FIG. 2B. In this case, the determination result in step S102 in FIG. 7 is affirmative, and then the determination results in steps S204 and S205 in FIG. 8 become affirmative within the predetermined time (Tmax). Thus, the treatment provider 7 is determined to have entered the room, causing the closed shutter 11 to be open.

The treatment provider 7 may move to a different position or may move to face in a different direction in the room 2a. In this case as well, at least one of the beacon detectors BD1 or BD2 can detect the beacon signal BC that may possibly be weak from the treatment provider 7. More specifically, at least one of the determination results in steps S306 or S307 in FIG. 9 can be negative. Thus, the treatment provider 7 is determined to be staying in the room 2a, and the shutter 11 remains open.

The treatment provider 7 then leaves the room 2a through the doorway 3 and walks down the corridor 1, moving away from the doorway 3. In this state, the beacon detectors BD1 and BD2 both do not even detect the weak radio waves, and the determination results in steps S306 and S307 in FIG. 9 can be both affirmative. Thus, the treatment provider 7 is determined to have left the room, causing the open shutter 11 to be closed. For this determination, the threshold Rth3 is set to a value less than the threshold Rth1, and the threshold Rth4 is set to a value less than the threshold Rth2.

The shutter controller 34 may not perform the determination shown in FIGS. 7 to 9, but may perform other determination as appropriate. For example, the shift to the open state may be performed based on a stateless condition, rather than a stateful condition, or specifically the condition using the ready state shown in FIG. 8. For example, the shift to the open state based on a stateless condition may be performed simply based on, for example, the condition RSSI(1)>threshold A and RSSI(2)>threshold B.

In this case, the shift condition may be satisfied by a limited small area in the room 2a. This can be, for example, a small area through which the treatment provider 7 moves from the doorway 3 toward the head of the treatment recipient 6. However, the treatment provider 7 may move from the doorway 3 toward the feet of the treatment recipient 6 without passing through this small area. Thus, a stateful shift condition such as the condition shown in FIGS. 7 and 8 may be used.

For example, the correspondence between the RSSI(1) and the RSSI(2) and the position and the facing direction of the treatment provider 7 in the room 2a may be mapped in advance. In this case, the shutter controller 34 determines the position and the facing direction of the treatment provider 7 based on the mapping information, and controls opening and closing of the shutter 11 based on the determination result. However, this method may involve creation of the mapping information and also complicate the position determination process based on the mapping information. Thus, a simple method, such as the method shown in FIGS. 7 to 9, may be used.

FIG. 10 is a flowchart of an example preprocess performed before the processes in FIGS. 7 to 9. First, a predetermined ID (IDx) is set for the transmitter TR (step S401). The IDx of the transmitter TR is set with the beacon detectors BD1 and BD2 (step S402). More specifically, for example, the IDx is stored into the memory 17 in the beacon detector BD1 and the memory 52 in the beacon detector BD2.

Subsequently, the owner carrying the transmitter TR is positioned at a predetermined position in the room 2a or on the corridor 1 in a predetermined direction (step S403). In this state, the beacon detector BD1 detects the RSSI(l) of the beacon signal BC including the IDx, and the beacon detector BD2 detects the RSSI(2) of the beacon signal BC including the IDx (step S404). The detected RSSI(1) and RSSI(2) are stored into, for example, the memory 17 in the monitoring device 10 (step S405).

The processing in steps S404 and S405 is repeatedly performed a predetermined number of times (step S406). This is performed for calculating, for example, the average values of the RSSI(1) and the RSSI(2) to reflect, for example, the instability of radio waves. The processing in steps S403 to S406 is repeatedly performed while changing the facing direction or the position of the owner until the processing is performed for all the predetermined positions and all the predetermined directions (step S407).

The RSSI map data representing the correspondence between the position and the facing direction of the owner faces and the RSSI(1) and the RSSI(2) is created through the processing in the steps S403 to S407. The thresholds Rth1 to Rth4 described with reference to FIGS. 7 to 9 are determined based on the RSSI map data (step S408). The determined thresholds Rth1 and Rth3 are stored into the memory 17 in the monitoring device 10. The determined thresholds Rth2 and Rth4 are stored into the memory 52 in the beacon detector BD2. The processing in step S408 is performed by, for example, a manager.

Modifications

Although the two beacon detectors are installed in the single room 2a in the example in FIG. 1, a smaller number of more than two beacon detectors may be installed depending on the size of the room 2a or the number of beds 5 in the room 2a. For example, when two beds are installed in the room 2a, three or more beacon detectors in total may be installed, including one beacon detector for detecting the RSSI(I) at the doorway 3 and two beacon detectors, one for detecting the RSSI(2) at one of the two beds 5 and the other for detecting an RSSI(3) at the other bed.

In this case, the determination as to whether to shift to the open state in step S205 in FIG. 8 may be based on the OR determination that the RSSI(2) is higher than the corresponding threshold or the RSSI(3) is higher than the corresponding threshold. In contrast, the determination as to whether to shift to the closed state in step S306 in FIG. 9 may be based on the AND determination that the RSSI(2) is lower than the corresponding threshold and the RSSI(3) is lower than the corresponding threshold. For any area in the room 2a in which no beacon detectors detect the beacon signal BC, an additional beacon detector may be installed to cover the area.

Advantages of Embodiments

The monitoring system according to the above embodiment includes two or more beacon detectors in a room, and can thus determine whether the treatment provider 7 is in the room with high accuracy and appropriately control the opening and closing of the shutter 11 based on the determination result. Thus, the monitoring system can monitor the treatment recipient 6 being treated when the treatment provider 7 is in the room, and can protect the privacy of the treatment recipient 6 when the treatment provider 7 is not in the room.

The monitoring system can be implemented at low cost. For example, many beacon detectors may be arranged in a mesh in a room to determine the position of the treatment provider 7 with high accuracy. However, this can increase the cost, and complicate the position determination process. In the embodiment described above, the determination is simply performed as to whether the treatment provider 7 is in the room, without involving highly accurate detection of the position of the treatment provider 7. The method in the embodiment thus uses a smaller number of more than two beacon detectors located in a room, thus reducing the cost. Simply comparing the RSSI with the thresholds simplifies the processes.

The present invention is not limited to the above embodiment, but may be modified variously without departing from the spirit and scope of the invention.

What is claimed is:

1. A monitoring system, comprising:
a transmitter to be carried by a treatment provider to treat a treatment recipient in a room;
a monitoring device placeable nearer a doorway of the room than a treatment location at which the treatment recipient is to be treated; and
a second beacon detector placeable nearer the treatment location than the monitoring device,
wherein the transmitter transmits a beacon signal,
the second beacon detector detects a second received signal strength indicator of the beacon signal from the transmitter, and
the monitoring device includes
an imaging element configured to capture an image of the treatment recipient being treated by the treatment provider through an opening,
an open-close body configured to open and close the opening,
a first beacon detector configured to detect a first received signal strength indicator of the beacon signal from the transmitter,
an obtainer configured to obtain the second received signal strength indicator detected by the second beacon detector, and
an open-close body controller configured to control opening and closing of the open-close body based on the first received signal strength indicator detected by the first beacon detector and the second received signal strength indicator obtained by the obtainer.

2. The monitoring system according to claim 1, wherein the open-close body controller controls the open-close body being closed to open in response to the first received signal strength indicator exceeding a first threshold and the second received signal strength indicator exceeding a second threshold within a predetermined time after the first received signal strength indicator exceeds the first threshold.

3. The monitoring system according to claim 1, wherein the open-close body controller controls the open-close body being open to close in response to the second received signal strength indicator falling below a fourth threshold and the first received signal strength indicator falling below a third threshold.

4. The monitoring system according to claim 1, wherein the open-close body controller controls the open-close body being closed to open in response to the first received signal strength indicator exceeding a first threshold and the second received signal strength indicator exceeding a second threshold within a predetermined time after the first received signal strength indicator exceeds the first threshold, and
controls the open-close body being open to close in response to the second received signal strength indicator falling below a fourth threshold and the first received signal strength indicator falling below a third threshold.

5. The monitoring system according to claim 4, wherein the third threshold is less than the first threshold, and the fourth threshold is less than the second threshold.

6. The monitoring system according to claim 1, wherein the beacon signal complies with a Bluetooth low energy standard.

\* \* \* \* \*